United States Patent

Olesen et al.

[11] Patent Number: 5,977,129
[45] Date of Patent: Nov. 2, 1999

[54] AZACYCLIC AND AZABICYCLIC SUBSTITUTED OXA- OR THIA-DIAZOLE COMPOUNDS

[75] Inventors: Preben H. Olesen, København; Per Sauerberg, Valby, both of Denmark

[73] Assignee: Novo Nordisk A/S, Bagsvaerd, Denmark

[21] Appl. No.: 08/999,973

[22] Filed: May 3, 1995

Related U.S. Application Data

[62] Division of application No. 08/000,055, Jan. 4, 1993, Pat. No. 5,414,009.

[30] Foreign Application Priority Data

Jan. 13, 1992 [DK] Denmark ................ PCT/DK92/00009

[51] Int. Cl.$^6$ ................ A61K 31/435; A61K 31/44; C07D 417/14; C07D 451/02
[52] U.S. Cl. ................ 514/299; 514/214; 514/305; 514/333; 514/362; 514/364; 540/461; 540/477; 540/582; 540/584; 546/112; 546/133; 546/137; 546/256; 548/135
[58] Field of Search ................ 546/256, 112, 546/133; 514/299, 333, 214, 305; 540/582, 461

[56] References Cited

U.S. PATENT DOCUMENTS

| | | | |
|---|---|---|---|
| 5,041,455 | 8/1991 | Sauerberg et al. | 514/342 |
| 5,043,345 | 8/1991 | Sauerberg et al. | 514/342 |

FOREIGN PATENT DOCUMENTS

| | | |
|---|---|---|
| 0 239 309 | 9/1987 | European Pat. Off. . |
| 0 244 018 | 11/1987 | European Pat. Off. . |
| 0 296 721 | 12/1988 | European Pat. Off. . |
| 0 301 729 | 2/1989 | European Pat. Off. . |
| 0 307 142 | 3/1989 | European Pat. Off. . |
| 0 316 718 | 5/1989 | European Pat. Off. . |
| 0 322 182 | 6/1989 | European Pat. Off. . |
| 0 328 200 | 8/1989 | European Pat. Off. . |
| 0 349 956 | 1/1990 | European Pat. Off. . |
| 0 384 285 | 8/1990 | European Pat. Off. . |
| 0 459 568 | 12/1991 | European Pat. Off. . |

OTHER PUBLICATIONS

Dunn PJ and Rees CW. J. Chem. Soc. Perkin Trans. 1 (12). 2489–94, 1989.

*Primary Examiner*—Evelyn Mei Huang
*Attorney, Agent, or Firm*—Steve T. Zelson, Esq.; Elais J. Lambiris, Esq.

[57] ABSTRACT

The present invention relates to compounds of formula I:

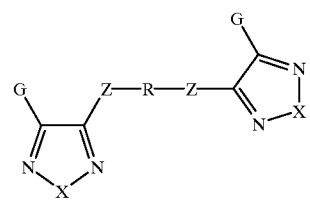

(I)

wherein
one or both G is an azacyclic ring of formula II:

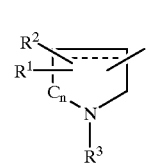

(II)

and Z is oxygen or sulfur and the remaining variables are as defined in the specification. The compounds are useful as stimulants of the cognitive function of the forebrain and hippocampus of mammals and especially in the treatment of Alzheimer's disease, severe painful conditions and glaucoma.

25 Claims, No Drawings

AZACYCLIC AND AZABICYCLIC SUBSTITUTED OXA- OR THIA-DIAZOLE COMPOUNDS

This is a divisional application of application Ser. No. 08/000,055, filed Jan. 4, 1993, U.S. Pat. No. 5,414,909 the contents of which are incorporated herein by reference in their entirety.

The present invention relates to therapeutically active azacyclic or azabicyclic compounds, a method of preparing the same and to pharmaceutical compositions comprising the compounds. The novel compounds are useful as stimulants of the cognitive function of the forebrain and hippocampus of mammals and especially in the treatment of Alzheimer's disease.

Due to the in general improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, a up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, then the postsynaptic muscarinic receptors in the forebrain and hippocampus still exist. Therefore muscarinic cholinergic agonists are useful in the treatment of Alzheimer's disease and in improving the cognitive functions of elderly people.

It is well known that arecoline (methyl 1-methyl-1,2,5,6-tetrahydropyridine-3-carboxylate) is such a cholinergic agonist.

Arecoline however has a very short biological half life and a small separation between central and peripheral muscarinic effects. Furthermore arecoline is a rather toxic compound.

It is an object of the invention to provide new muscarinic cholinergic compounds.

The novel compounds of the invention are heterocyclic compounds having the formula I

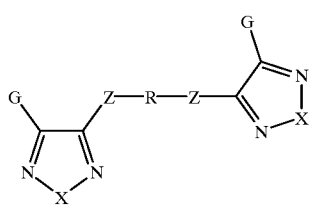

(I)

wherein X and Z independently are oxygen or sulfur; and C is independently selected from the group of azacyclic or azabicyclic ring systems consisting of

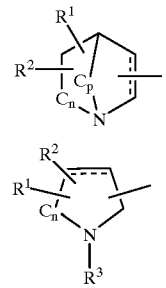

wherein
the oxadiazole or thiadiazole ring can be attached at any position; and
$R^1$ and $R^2$ may be present at any position, including the point of attachment of the oxadiazole or thiadiazole ring, and independently are H, straight or branched $C_{1-5}$-alkyl, straight or branched $C_{2-6}$-alkenyl, straight or branched $C_{2-6}$-alkynyl, straight or branched $C_{1-6}$-alkoxy, straight or branched $C_{1-6}$-alkyl substituted with hydroxy, hydroxy, halogen, amino or carboxy; and
$R^3$ is H, straight or branched $C_{1-5}$-alkyl, straight or branched $C_{2-5}$-alkenyl or straight or branched $C_{2-5}$-alkynyl; and
n and p independently are 1, 2 or 3; and

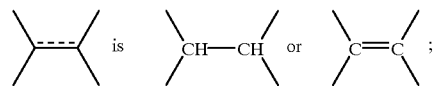

and
R is straight or branched $C_{1-10}$-alkylene, straight or branched $C_{2-10}$-alkenylene, straight or branched $C_{2-10}$-alkynylene, $C_{3-8}$-cycloalkylene or $R^4$—$R^5$—$R^6$ wherein $R^4$ and $R^6$ independently are straight or branched $C_{1-5}$-alkylene, straight or branched $C_{2-5}$-alkenylene or straight or branched $C_{2-5}$-alkynylene, and $R^5$ is $C_{3-8}$-cycloalkylene,

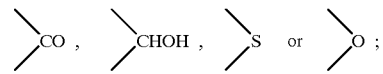

or a pharmaceutically acceptable salt thereof or a prodrug thereof.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts.

Preferred values for n and p independently are 1 and 2.

Specific compounds within the scope of the present invention include the following, and pharmaceutically acceptable salts and prodrugs thereof:

1,4-Bis(3-(exo-1-azabicyclo[3.2.1]octan-6-yl)-1,2,5-thiadiazol-4-ylthio)butane 1,5-Bis(3-(exo-1-azabicyclo[3.2.1]octan-6-yl)-1,2,5-thiadiazol-4-ylthio)pentane 1,4-Bis(3-(exo-1-azabicyclo[2.2.1]heptan-3-yl)-1,2,5-thiadiazol-4-ylthio)pentane 1,5-Bis(3-(exo-1-azabicyclo[2.2.1]heptan-3-yl)-1,2,5-thiadiazol-4-ylthio)pentane 1-(3-(exo-1-azabicyclo[3.2.1]octan-6-yl)-1,2,5-thiadiazol-4-ylthio)-4-(3-(endo-1-azabicyclo[3.2.1]octan-6-yl)-1,2,5-thiadiazol-4-ylthio)butane 1-(3-(exo-1-azabicyclo[3.2.1]octan-6-yl)-1,2,5-thiadiazol-4-ylthio)-4-(3-(1-methyl-1,2,5,6-tetrahydropyridin-3-yl)-1,2,5-thiadiazol-4-ylthio)butane 1-(3-(exo-1-azabicyclo[2.2.1]heptan-3-yl)-1,2,5-thiadiazol-4-ylthio)-4-(3-(endo-1-azabicyclo[2.2.1]heptan-3-yl)-1,2,5-thiadiazol-4-ylthio)butane 1,4-Bis(3-(endo-1-azabicyclo[2.2.1]heptan-3-yl)-1,2,5-thiadiazol-4-ylthio)butane 1-(3-exo-1-azabicyclo[2.2.1]heptan-3-yl)1,2,5-thiadiazol-4-ylthio)-4-(3-(endo-1-azabicyclo[3.2.1]octan-6-yl)-1,2,5-thiadiazol-4-ylthio)butane 1-(3-(exo-1-azabicyclo[2.2.1]heptan-3-yl)-1,2,5-thiadiazol-4-ylthio)-4-(3-exo-1-azabicyclo[3.2.1]octan-6-yl)-1,2,5-thiadiazol-4-ylthio)butane 1-(3-exo-1-azabicyclo[2.2.1]heptan-3-yl)-1,2,5-thiadiazol-4-ylthio)-4-(3-(1-methyl-1,2,5,6-tetrahydropyridin-3-yl)-1,2,5-thiadiazol-4-ylthio)butane 1-(3-(endo-1-azabicyclo[2.2.1]heptan-3-yl)-1,2,5-thiadiazol-4-ylthio)-4-(3-(endo-1-azabicyclo[3.2.1]octan-6-yl)-1,2,5-thiadiazol-4-ylthio)butane 1-(3-(endo-1-azabicyclo[2.2.1]heptan-3-yl)-1,2,5-thiadiazol-4-ylthio)-4-(3-exo-1-azabicyclo[3.2.1]octan-6-yl)-1,2,5-thiadiazol-4-ylthio)butane 1-(3-(endo-1-azabicyclo[2.2.1]heptan-3-yl)-1,2,5-thiadizaol-4-ylthio)-4-(3-(1-methyl-1,2,5,6-tetrahydropyridin-3-yl)-1,2,5-thiadiazol-4-ylthio)butane 1,4-Bis(3-(1-azabicyclo[2.2.2]octan-3-yl)-1,2,5-thiadiazol-4-ylthio)butane 1-(3-exo-1-azabicyclo[3.2.1]octan-6-yl)-1,2,5-thiadiazol-4-ylthio)-4-(3-(1-azabicyclo[2.2.2]octan-3-yl)-1,2,5-thiadiazol-4-ylthio)butane 1-(3-(1-azabicyclo[2.2.2]octan-3-yl)-1,2,5-thiadiazol-4-ylthio)-4-(3-(1-methyl-1,2,5,6-tetrahydropyridin-3-yl)-1,2,5-thiadiazol-4-ylthio)butane 1-(3-(1-Azabicyclo[2.2.2]octan-3-yl)-1,2,5-thiadiazol-4-ylthio)-4-(3-(exo-1-azabicyclo[2.2.1]heptan-3-yl)-1,2,5-thiadiazol-4-ylthio)butane.

The compounds of this invention are also useful analgesic agents and therefore useful in the treatment of severe painful conditions.

Furthermore, the compounds of this invention are useful in the treatment of glaucoma.

The invention also relates to methods of preparing the above mentioned compounds, comprising:

reacting a compound of formula II

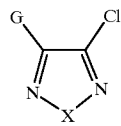

(II)

wherein G and X have the meanings defined above, with an appropriate dinucleophile to give compounds of formula I wherein Z is S or O.

It is to be understood that the invention extends to each of the stereoisomeric forms of the compounds of formula I as well as the racemates.

The pharmacological properties of the compounds of the invention can be illustrated by determining their capability to inhibit the specific binding of $^3$H-Oxotremorine-M ($^3$H-Oxo). Birdsall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-Oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 s in 10 ml 20 mM Hepes pH; 7.4, with an Ultra-Turrax homogenizer. The homogenizer is rinsed with 10 ml of buffer and the combined suspension centrifuged for 15 min. at 40,000×g. The pellet is washed three times with buffer. In each step the pellet is homogenized as before in 2×10 ml of buffer and centrifuged for 10 min. at 40,000×g.

The final pellet is homogenized in 20 mM Hepes pH: 7.4 (100 ml per g of original tissue) and used for binding assay. Aliquots of 0.5 ml is added 25 ul of test solution and 25 ul of $^3$H-Oxotremorine (1.0 nM, final concentration) mixed and incubated for 30 min. at 25° C. Non-specific binding is determined in triplicate using arecoline (1 ug/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steam-bath for less than 5 min.) at a concentration of 2.2 mg/ml. 25–75% inhibition of specific binding must be obtained before calculation of $IC_{50}$. The test value will be given as $IC_{50}$ (the concentration (ng/ml) of the test substance which inhibits the specific binding of $^3$H-Oxo by 50%).

$IC_{50}$=(applied test substance concentration)

$$IC_{50} = \text{(applied test substance concentration)} \times \frac{1}{\left(\frac{C_o}{C_x} - 1\right)} \text{ng/ml}$$

where $C_o$ is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$H-PRZ (pirenzepine, [N-methyl-$^3$H]) binding to rat cerebral cortex membranes.

Pirenzepine binds selectively to subtype of muscarinic receptors. Historically the type is names the $M_1$-site, whereas pirenzepine sensitive site would be more appropriate. Although selective for $M_1$-sites pirenzepine also interact with $M_2$-sites.

All preparations are performed at 0–4° C. unless otherwise indicated. Fresh cortex (0.1–1 g) from male Wistar rats (150–200 g) is homogenized for 5–10 s. in 10 ml 20 mM Hepes pH: 7.4, with an Ultra-Turrax homogenizer. The homogenizer is rinzed with 2×10 ml of buffer and the combined suspension centrifuged for 15 min at 40,000×g. The pellet is washed three times with buffer. In each step the pellet is homogenized as before in 3×10 ml of buffer and centrifuged for 10 min at 40,000×g.

The final pellet is homogenized in 20 mM Hepes pH: 7.4 (100 ml per g of original tissue) and used for binding assay. Aliquots of 0.5 ml is added 20 μl of test solution and 25 μl of ³H-Pirenzepine (1.0 nM, final conc.), mixed and incubated for 60 min at 20° C. Non-specific binding is determined in triplicate using atropine (1 μg/ml, final conc.) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus no-specific binding.

Test substances are dissolved in 10 ml water, at a concentration of 0.22 mg/ml. 25–75% inhibition of specific binding must be obtained before calculation of $IC_{50}$.

The test value will be given as $IC_{50}$ (the concentration, ng/ml) of the test substance which inhibits the specific binding of ³H-PRZ by 50%.

$IC_{50}$=(applied test substance concentration)

$$IC_{50} = \text{(applied test substance concentration)} \times \frac{1}{\left(\frac{C_o}{C_x} - 1\right)} \text{ng/ml}$$

where $C_o$ is specific binding in control assays and $C_x$ is the specific binding in the test assay. (The calculations assume normal mass-action kinetics).

Test results obtained by testing some compounds of the present invention will appear from the following table 1.

TABLE 1

| | $IC_{50}$, nM | |
|---|---|---|
| Compound | ³H-Oxo-M | ³H-P2 |
| 1 | 15 | 12 |
| 2 | 2.9 | 1.7 |
| 3 | 6.1 | 15 |
| 4 | 5.2 | 9.8 |
| 5 | 5.9 | 0.9 |
| 6 | 21.0 | 5.3 |
| 7 | 1.9 | 0.48 |
| 8 | 4.3 | 8.0 |

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxy-methylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 1–100 mg in a pharmaceutically-acceptable carrier per unit dosage.

The dosage of the compounds according to this invention is 1–100 mg/day, preferably 10–70 mg/day, when administered to patients, e.g. humans, as a drug.

A typical tablet which may be prepared by conventional tabletting techniques contains:

| | |
|---|---|
| Active compound | 5.0 mg |
| Lactosum | 67.8 mg Ph. Eur. |
| Avicel ® | 31.4 mg |
| Amberlite ® | 1.0 mg |
| Magnesii stearas | 0.25 mg Ph. Eur. |

Due to the high muscarinic cholinergic receptor agonistic activity, the compounds of the invention are extremely useful in the treatment of symptoms related to a reduction of the cognitive functions of the brain of mammals, when administered in an amount effective for stimulating the cognitive functions of the forebrain and hippocampus. The important stimulating activity of the compounds of the invention includes both activity against the pathophysiological disease, Alzheimer's disease as well as against normal degeneration of brain function. The compounds of the invention may accordingly be administered to a subject, e.g., a living animal body, including a human, in need of stimulation of the cognitive functions of the forebrain and hippocampus, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective forebrain and hippocampus stimulating amount, and in any event an amount which is effective for improving the cognitive function of mammals due to their muscarinic cholinergic receptor agonistic activity. Suitable dosage ranges are 1–100 milligrams daily, 10–100 milligrams daily, and especially 30–70 milligrams daily, depending as usual upon the exact mode of administration, form in which administered, the indication towards which the administration is directed, the subject involved and the body weight of the subject involved, and the preference and experience of the physician or veterinarian in charge.

The invention will now be described in further detail with reference to the following examples:

EXAMPLE 1

1,3-Bis(3-(1-methyl-1,2,5,6-tetrahydropyridin-3-yl)-1,2,5-thiadiazol-4-ylthio)propane dioxalate (Compound 1)

To a solution of 3-(3-Chloro-1,2,5-thiadiazol-4-yl)-1,2,5,6-tetrahydro-1-methylpyridine (EPA No. 90102913.2) (640 mg, 3mmol) in DMF (20 ml) was added NaSH,$H_2O$ (370 mg, 4mmol) and the reaction mixture was stirred at room temperature for 1 h. $K_2CO_3$ (1.5 g, 10 mmol) and then 1,3-diiodopropane (445 mg, 1.5 mmol) was added to the reaction mixture and the reaction was stirred for 18 h. Water was added and the mixture was extracted with methylene chloride (3×150 ml). The dried and evaporated organic phases were purified by column chromatography (eluent: methanol: methylene Chloride (1:9)). The free base of the title compound was isolated as an oil in 430 mg (0.9 mmol) yield. Crystallization with oxalic acid (166 mg, 1.8 mmol) from acetone gave the title compound, which after recrystallization from ethanol was isolated in 480 mg (50%) yield. M.p. 125–127° C. MS: 466 ($M^+$).

The following compounds were made in exactly the same manner using the appropriate alkyldihalogenide:

1,4-Bis(3-(1-methyl-1,2,5,6-tetrahydropyridin-3-yl)-1,2,5-thiadiazol-4-ylthio)butane dioxalate (Compound 2). M.p. 163–165° C. MS: 480 $M^+$).

1,5-Bis(3-(1-methyl-1,2,5,6-tetrahydropyridin-3-yl)-1,2,5-thiadiazol-4-ylthio)pentane dioxalate (Compound 3). M.p. 152–153° C. MS: 494 ($M^+$).

1,6-Bis(3-(1methyl-1,2,5,6-tetrahydropyridin-3-yl)-1,2,5-thiadiazol-4-ylthio)hexane dioxalate (Compound 4). M.p. 185–187° C. MS: 508 ($M^+$).

1,4-Bis(3-(1-methyl-1,2,5,6-tetrahydropyridine-3-yl)-1,2,5-thiadiazol-4-ylthio)-2-butyne dioxalate (Compound 8). M.p. 182–184° C. MS: 476 ($M^+$).

EXAMPLE 2

1,4-Bis(3-(endo(±)-1-azabicyclo[3.2.1]octan-6-yl)-1,2,5-thiadiazol-4-ylthio)butane dioxalate (Compound 5)

To a solution of endo (±) 6-(3-chloro-1,2,5-thiadiazol-4-yl)-1-azabicyclo[3.2.1]octane (PCT/DK91/00236) (0.33 g, 1.5 mmol) in DMF (30 ml) under $N_2$ was added NaSH,$H_2O$ (370 mg, 4 mmol) and the reaction mixture was stirred at room temperature for 1 h. $K_2CO_3$ (1.5 g, 10 mmol) was added. A solution of 1,4-dibromobutane (0.9 g, 4.2 mmol) in DMF (10 ml) was added dropwise over 1 h, and the reaction mixture was stirred at room temperature for another hour. The reaction mixture was poured on a 1N HCl solution (150 ml) and extracted with ether (2×50 ml). The water phase was basified with solid $K_2CO_3$ and extracted with ether (3×50 ml). The last ether extracts were combined and dried over $MgSO_4$. After evaporation, the residue was crystallized with oxalic acid in acetone giving the title compound in 300 mg (76%) yield. M.p. 169–171°. MS: 508 ($M^+$).

The following compound was made in exactly the same manner using the appropriate alkyldihalogenide:

1,5-Bis(3-(endo(±)-1-azabicyclo[3.2.1]octan-6yl)-1,2,5-thiadiazol-4ylthio))-3-methylpentane dioxalate (Compound 6). M.p. 118–120° C. MS: 536 ($M^+$).

EXAMPLE 3

1-(3-(endo(±)1-azabicyclo[3.2.1]octan-6-yl)-1,2,5-thiadiazol-4-ylthio)-4-(3-(1-methyl-1,2,5,6-tetrahydropyridin-3-yl)-1,2,5-thiadiazol-4-ylthio) butane dihydrochloride (Compound 7)

To a solution of endo (±) 6-(3-chloro-1,2,5-thiadiazol-4-yl)-1-azabicyclo[3.2.1]octane (PCT/DK91/00236) (0.33 g, 1.5 mmol) in DMF (30 ml) under $N_2$ was added NaSH,$H_2O$ (370 mg, 4 mmol) and the reaction mixture was stirred at room temperature for 1 h. $K_2CO_3$ (1.5 g, 10 mmol) and 3-(3-(4-chlorobutylthio)-1,2,5-thiadiazol-4-yl)-1,2,5,6-tetrahydro-1-methylpyridine oxalate (EPA No. 90102913.2) (2.0 g, 5 mmol) was added and the reaction mixture stirred overnight. The mixture was poured on water (200 ml) and extracted with ether (3×75 ml). The dried and evaporated organic phases were purified by column chromatography (eluent: $CH_2Cl_2$: MeOH:25% $NH_3$, 8:2:0.5%). The free base of the title compound was crystallized with hydrochloric acid in ether/ethanol as the dihydrochloride in 400 mg (60%) yield. M.p. 125–128° C. MS: 494 ($M^+$).

EXAMPLE 4

1,4-Bis(3-((±)-1-azabicyclo[2.2.2]octan-3-yl)-1,2,5-thiadiazol-4-ylthio)butane dihydrochloride (Compound 9)

To a solution of 3-(3-chloro-1,2,5-thiadiazol-4-yl)-1-azabicyclo[2.2.2]octane (1.4 g, 6 mmol) in DMF (10 ml) was added NaSH, $H_2O$ (780 mg, 8.4 mmol) and $K_2CO_3$ (2 g, 14.5 mmol). The reaction mixture was stirred at room temperature for 4 h and then 1,4-diiodobutane (940 mg, 3 mmol) was added. The reaction mixture was stirred at room temperature for 4 days. Water (10 ml) followed by ether (50 ml) was added to the reaction mixture and the precipitate was collected by filtration from the heterogenic mixture (free base of product). The solid was dissolved in 1M HCl (5 ml) and evaporated. Recrystallization from ethanol/ether gave the wanted product in 410 mg yield. M.p. 112–116° C. MS: 508 ($M^+$)

We claim:

1. A compound of formula I

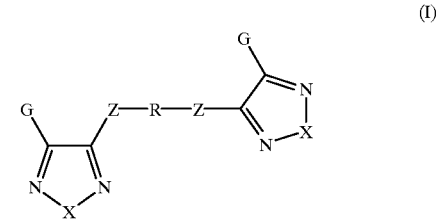

(I)

wherein

X is independently oxygen or sulfur resulting in the formation of an oxadiazole or thiadiazole ring;

Z is independently oxygen or sulfur;

R is straight or branched $C_{1-10}$-alkylene, straight or branched $C_{2-10}$-alkenylene, straight or branched $C_{2-10}$-alkynylene, $C_{3-8}$-cycloalkylene or $R^4$—$R^5$—$R^6$ wherein $R^4$ and $R^6$ independently are straight or branched $C_{1-5}$-alkylene, straight or branched $C_{2-5}$- alkenylene or straight or branched $C_{2-5}$-alkenylene, and $R^5$ is $C_{3-8}$-cycloalkylene, CO, CHOH, S or O; and G is an azacyclic ring of formula II:

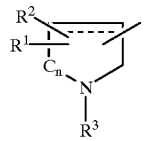

(II)

wherein
the oxadiazole or thiadiazole ring can be attached at any position of the azacyclic ring;
$R^1$ and $R^2$ independently are H, straight or branched $C_{1-5}$-alkyl, straight or branched $C_{2-5}$-alkenyl, straight or branched $C_{2-5}$-alkynyl, straight or branched $C_{1-5}$-alkoxy, hydroxy, halogen, amino, carboxy or straight or branched $C_{1-6}$-alkyl substituted with hydroxy;
$R^3$ is H, straight or branched $C_{1-5}$-alkyl, straight or branched $C_{2-5}$-alkenyl or straight or branched $C_{2-5}$-alkynyl;
n is 1, 2, or 3; and

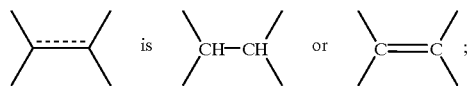

or a pharmaceutically acceptable salt thereof.

2. A compound according to claim 1, wherein n is 1.
3. A compound according to claim 2, wherein X and Z are sulfur.
4. A compound according to claim 2, wherein R is $C_{1-10}$-alkylene.
5. A compound according to claim 2, wherein $R^1$ and $R^2$ are independently H or $C_{1-5}$-alkyl.
6. A compound according to claim 3, wherein R is $C_{1-10}$-alkylene; and $R^1$ and $R^2$ are independently H or $C_{1-5}$-alkyl.
7. A compound according to claim 1, wherein n is 2.
8. A compound according to claim 7, wherein X and Z are sulfur.
9. A compound according to claim 7, wherein R is $C_{1-10}$-alkylene.
10. A compound according to claim 7, wherein $R^1$ and $R^2$ are independently H or $C_{1-5}$-alkyl.
11. A compound according to claim 8, wherein R is $C_{1-10}$-alkylene; and $R^1$ and $R^2$ are independently H or $C_{1-5}$-alkyl.
12. A compound according to claim 1, wherein n is 3.
13. A compound according to claim 12, wherein X and Z are sulfur.
14. A compound according to claim 12, wherein R is $C_{1-10}$-alkylene.
15. A compound according to claim 12, wherein $R^1$ and $R^2$ are independently H or $C_{1-5}$-alkyl.
16. A compound according to claim 13, wherein R is $C_{1-10}$-alkylene; and $R^1$ and $R^2$ are independently H or $C_{1-5}$-alkyl.
17. A compound according to claim 1 which is
1,3-Bis(3-(1-methyl-1,2,5,6-tetrahydropyridin-3-yl)-1,2,5-thiadiazol-4-ylthio) propane;
1,4-Bis(3-(1-methyl-1,2,5,6-tetrahydropyridin-3-yl)-1,2,5-thiadiazol-4-ylthio) butane;
1,5-Bis(3-(1-methyl-1,2,5,6-tetrahydropyridin-3-yl)-1,2,5-thiadiazol-4-ylthio) pentane;
1,6-Bis(3-(1-methyl-1,2,5,6-tetrahydropyridin-3-yl)-1,2,5-thiadiazol-4-ylthio) hexane;
1,4-Bis(3-(1-methyl-1,2,5,6-tetrahydropyridine-3-yl)-1,2,5-thiadiazol-4-ylthio)-2butyne; or
a pharmaceutically acceptable salt or prodrug thereof.

18. A pharmaceutical composition comprising a compound according to claim 1 together with a pharmaceutically acceptable carrier or diluent.
19. The pharmaceutical composition according to claim 18 in the form of an oral dosage unit or parenteral dosage unit.
20. The pharmaceutical composition according to claim 19, wherein said dosage unit comprises from about 1 to about 100 mg of the compound.
21. A pharmaceutical composition for stimulating the cognitive functions of the forebrain and hippocampus of mammals, treating Alzheimer's disease or glaucoma or providing an analgesic effect, comprising an effective amount of a compound according to claim 1 together with a pharmaceutically acceptable carrier or diluent.
22. A compound of formula I

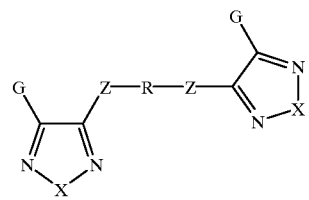

(I)

wherein
X is independently oxygen or sulfur resulting in the formation of an oxadiazole or thiadiazole ring;
Z is independently oxygen or sulfur;
R is straight or branched $C_{1-10}$-alkylene, straight or branched $C_{2-10}$-alkenylene, straight or branched $C_{2-10}$-alkynylene, $C_{3-8}$-cycloalkylene or $R^4$—$R^5$—$R^6$ wherein $R^4$ and $R^6$ independently are straight or branched $C_{1-5}$-alkylene, straight or branched $C_{2-5}$-alkenylene or straight or branched $C_{2-5}$-alkenylene, and $R^5$ is $C_{3-8}$-cycloalkylene, CO, CHOH, S or O; and
one G is an azacyclic ring of formula II and the second G is an azabicyclic ring of formula III:

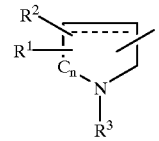

(II)

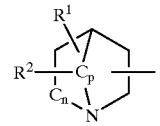

(III)

wherein
the oxadiazole or thiadiazole ring can be attached at any position of the azacyclic and azabicyclic ring;

R¹ and R² independently are H, straight or branched $C_{1-5}$-alkyl, straight or branched $C_{2-5}$-alkenyl, straight or branched $C_{2-5}$-alkynyl, straight or branched $C_{1-5}$-alkoxy, hydroxy, halogen, amino, carboxy or straight or branched $C_{1-6}$-alkyl substituted with hydroxy;

R³ is H, straight or branched $C_{1-5}$-alkyl, straight or branched $C_{2-5}$-alkenyl or straight or branched $C_{2-5}$-alkynyl;

n and p independently are 1, 2, or 3; and

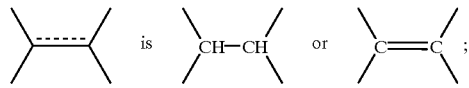

or a pharmaceutically acceptable salt thereof.

23. A compound according to claim 22 which is 1-(3-(endo(±)-1-azabicyclo [3.2.1]octan-6-yl)-1,2,5-thiadiazol-4-ylthio)-4-(3-(1-methyl-1,2,5,6-tetrahydropyridin-3-yl)-1,2,5-thiadiazol-4-ylthio) butane or a pharmaceutically acceptable salt thereof.

24. A pharmaceutical composition comprising a compound according to claim 22 together with a pharmaceutically acceptable carrier or diluent.

25. The pharmaceutical composition according to claim 24 in the form of an oral dosage unit or parenteral dosage unit.

* * * * *